(12) United States Patent
Wu et al.

(10) Patent No.: US 11,782,067 B2
(45) Date of Patent: Oct. 10, 2023

(54) BIOLOGIC SAMPLE PREPARATION SYSTEM AND RELATED METHOD

(71) Applicant: SM RESEARCH INC., Richmond Hill (CA)

(72) Inventors: Yuan Min Wu, Richmond Hill (CA); Yuanji Chen, Richmond Hill (CA); Chaojun Zhou, Richmond Hill (CA); Yu Qin, Richmond Hill (CA); Zonghua Liu, Scarborough (CA); Eileen Xiao Feng Nie, Richmond Hill (CA); Tao Chen, Richmond Hill (CA)

( * ) Notice: Subject to any disclaimer, the term of this patent is extended or adjusted under 35 U.S.C. 154(b) by 919 days.

(21) Appl. No.: 16/461,565

(22) PCT Filed: Nov. 18, 2016

(86) PCT No.: PCT/IB2016/001641
§ 371 (c)(1),
(2) Date: May 16, 2019

(87) PCT Pub. No.: WO2018/091938
PCT Pub. Date: May 24, 2018

(65) Prior Publication Data
US 2019/0369134 A1    Dec. 5, 2019

(51) Int. Cl.
*G01N 35/10* (2006.01)
*G01N 1/28* (2006.01)
(Continued)

(52) U.S. Cl.
CPC ...... *G01N 35/1065* (2013.01); *B01L 3/50857* (2013.01); *B01L 7/04* (2013.01);
(Continued)

(58) Field of Classification Search
None
See application file for complete search history.

(56) References Cited

U.S. PATENT DOCUMENTS 6,589,483 B1 *  7/2003  Maeda ............... G01N 35/1065
                                                73/863.25
6,627,446 B1 *  9/2003  Roach .............. G01N 27/44791
                                                436/514
(Continued)

FOREIGN PATENT DOCUMENTS

CA    2864260 A1 *  8/2013  ............... G01N 1/28
EP    2754496 A2 *  7/2014  ............... B01L 3/00

*Primary Examiner* — Brian R Gordon
(74) *Attorney, Agent, or Firm* — Nasser Ashgriz; UIPatent Inc.

(57) ABSTRACT

A biologic sample preparation system that prepares samples for processing includes a frame defining a horizontal plane, a pipette assembly, a sample module and an extraction module. The pipette assembly includes a first pipette. The pipette assembly is movably mounted to the frame in a direction substantially perpendicular to the horizontal plane during operation. The sample module includes a sample plate and is movably mounted to the frame. The sample module is movable substantially parallel to the horizontal plane at least from a sample area spaced from the pipette assembly and a working area proximate the pipette assembly. The extraction module includes an extraction plate and is movably mounted to the frame. The extraction module is movable substantially parallel to the horizontal plane at least from an extraction staging area spaced from the pipette, assembly and the working area proximate the pipette assembly.

5 Claims, 13 Drawing Sheets

(51) Int. Cl.
*B01L 7/04* (2010.01)
*B01L 3/00* (2006.01)
*C12Q 1/6806* (2018.01)
*G01N 35/00* (2006.01)

(52) U.S. Cl.
CPC ............ *C12Q 1/6806* (2013.01); *G01N 1/28* (2013.01); *B01L 2200/10* (2013.01); *B01L 2200/16* (2013.01); *B01L 2300/0609* (2013.01); *B01L 2300/1883* (2013.01); *B01L 2400/088* (2013.01); *G01N 2035/00356* (2013.01); *G01N 2035/1053* (2013.01)

(56) References Cited

U.S. PATENT DOCUMENTS

| | | | | |
|---|---|---|---|---|
| 6,734,424 B2* | 5/2004 | Lennon | ................ | B01L 3/0262 73/864.22 |
| 7,025,933 B2* | 4/2006 | Ganz | ..................... | G01N 1/312 422/68.1 |
| 7,585,463 B2* | 9/2009 | Austin | ............... | G01N 35/1009 422/65 |
| 2002/0142483 A1* | 10/2002 | Yao | ...................... | B01L 3/0248 422/63 |
| 2003/0124735 A1* | 7/2003 | Nanthakumar | .... | G01N 35/1065 506/40 |
| 2006/0002824 A1* | 1/2006 | Chang | ................ | G01N 35/1016 422/400 |
| 2007/0077645 A1* | 4/2007 | Aoyagi | ............. | G01N 35/1065 435/287.2 |
| 2010/0137165 A1* | 6/2010 | Tajima | ............... | G01N 35/0098 506/40 |
| 2013/0029856 A1* | 1/2013 | Kelso | ................. | G01N 35/1011 435/6.12 |
| 2015/0260747 A1* | 9/2015 | Samsoondar | ......... | B01L 3/0237 422/511 |

* cited by examiner

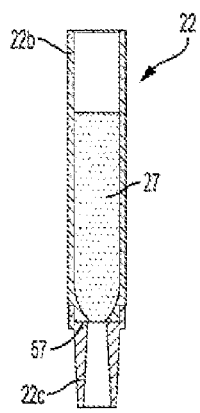 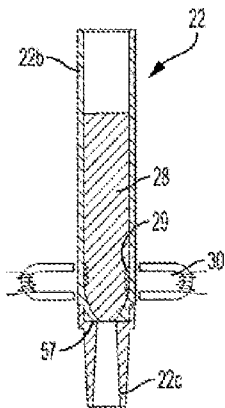
FIG. 9A  FIG. 9B
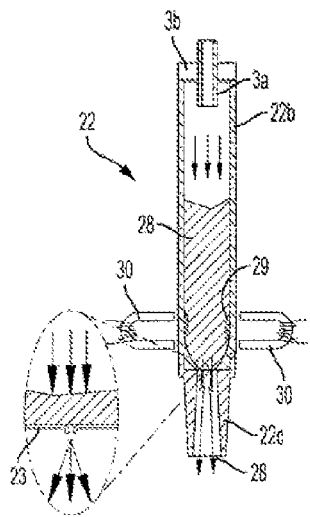 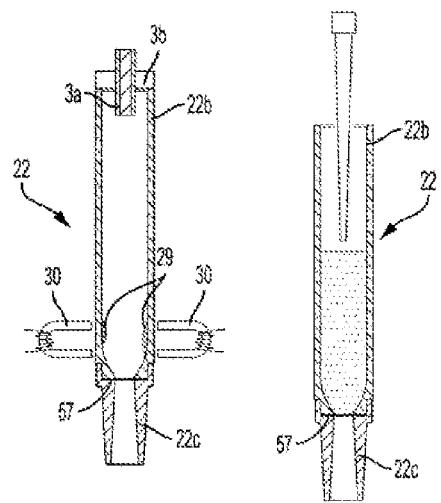
FIG. 9C  FIG. 9D  FIG. 9E

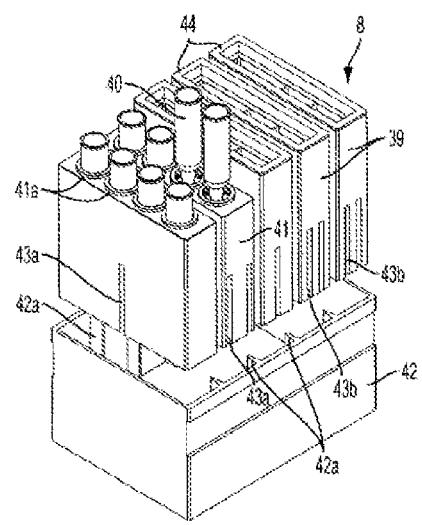
FIG. 12
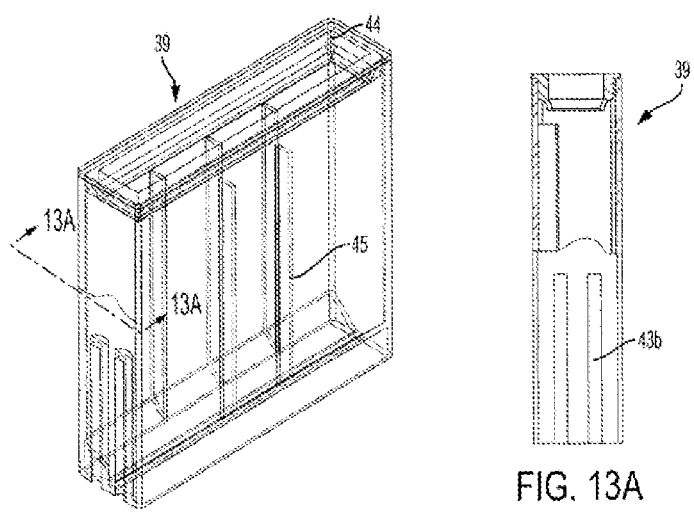
FIG. 13
FIG. 13A

BIOLOGIC SAMPLE PREPARATION SYSTEM AND RELATED METHOD

BACKGROUND OF THE INVENTION

Biologic sample preparation for analytic processing systems involves manipulation and processing of multiple biologic samples in a substantially sterile environment. It is important to process the samples without contamination or results will be inaccurate, compromised and potentially lead to false positive in subsequent analytic processing and testing. Samples can be prepared for numerous analytic processing systems and techniques, such as a polymerase chain reaction ("PCR") system. PCR is a technique used in molecular biology to amplify a single copy or a few copies of a piece of nucleic acid such as deoxyribonucleic acid ("DNA) or ribonucleic acid ("RNA"), across several orders of magnitude, generating thousands to millions of copies of a particular sequence. PCR is typically considered an easy and cheap tool to amplify a focused segment of nucleic acid, useful in the diagnosis and monitoring of genetic diseases, identification of criminals (under the field of forensics), studying the function of targeted segment, and other related uses. PCR is an example of an analytic processing technique or system that the sample preparation system of the present invention works in concert with by preparing samples that are utilized in the analytic processing systems. Another example of an analytic processing system that may utilize samples prepared by the preferred system is enzyme-linked immunosorbent assay ("ELISA"), which detects antigen or antibody for immunology and toxicology. Purity of the biologic samples is important for these analytic processing systems to produce accurate results in the subsequent analytic processing systems.

A problem with preparation of samples for analytic processing systems, such as PCR, is that the preparation process risks contamination when the amplification vessels are open, and the samples are being prepared. Spillage, droplet formation and/or aerosols can be generated when the caps are removed in order to remove a portion of the amplified reaction product for detection analysis. Cross contamination can also occur during introduction and removal of a pipette from the system due to the movement of the contaminated pipettes above open sample containers. This can spread the amplified product throughout the lab by airborne droplets or on equipment and can contaminate un-amplified samples and reagents. Such contamination will quickly lead to false positive results or erroneous and incorrect test results. Care must be taken to prevent such contamination. Physical separation between sample preparation, amplification and detection areas has been customarily used to limit contamination between samples and from the surrounding environment. Such measures are quite cumbersome, expensive and require rigorous training to prevent transfer of materials to lab coats, gloves, pipettes or laboratory equipment between such segregated areas.

Referring to FIG. 1, a portion of a prior art biologic material handling system includes a moving pipette assembly 180 with several individual pipettes 180a, 180b, 180c, 180d, 180e, 180f, 180g, 180h. The pipette assembly 180 is mounted to a movable robotic frame 181 that is movable in longitudinal and lateral directions X, Y relative to a sample tray 182 including sample tubes 183 that are preferably loaded with biological materials, such as whole blood, serum, or other biological materials for nucleic acid amplification. The pipettes 180a-180h are also preferably movable in a vertical direction Z relative to the robotic frame 181. In operation, the sample tray 182 is held in place while the robotic frame 181 moves relative to the sample tray 182 for sampling purposes. The numerous stops and starts of the pipette assembly 180 over the sample tubes 183, often after the pipettes 180a-180h are placed into contact with the samples in the sample tubes 183, results in extensive potential contamination of all of the samples on the sample tray 182 when the robotic frame 181 moves, starts, stops and vibrates over the sample tubes 183 creating potential for cross-contamination and failure of the expensive and precise testing. It is desirable to design, implement and deploy a sample handling system that reduces or eliminates the risk of cross-contamination created when the contaminated pipettes, 180a-180h move, stop and start under potential vibratory loads over the sample tray 182. The sample tubes 183 also require the samples and other materials, such as buffers, in the sample tubes 183 to enter and exit through a top opening, which further creates potential contamination issues. The preferred present invention addresses these deficiencies of the prior art biologic material handling systems by reducing the movement of pipettes over the samples and utilizing tubes that permit one-way flow of fluids therein.

BRIEF SUMMARY OF THE INVENTION

The preferred invention is directed to a biologic sample preparation system that prepares samples for analytic processing. The preferred sample preparation system is able to isolate liquid phase biological molecules. The samples may be prepared for detecting or quantifying biological molecules, such as DNA or RNA, in biological samples, for example by PCR processes, including digital-PCR processes, for amplifying nucleic acids. The samples may also be prepared for isolating or analyzing peptides, proteins, plasmid or chromosomal DNA, mRNA or other biological molecules of interest by other processing, such as an immunoassay (e.g., an ELISA, immunofluorescence assay), nucleic acid hybridization, fluorescence spectroscopy, chemiluminescence assay, etc. The preferred biologic sample preparation system includes a frame defining a substantially horizontal plane, a pipette assembly including a pipette, a sample module including a sample plate and an extraction module including an extraction plate. The pipette assembly is movably mounted to the frame and is movable only in a direction substantially perpendicular to horizontal plane during operation. A sample module is movably mounted to the frame. The sample module is movable substantially parallel to the horizontal plane at least from a sample area spaced from the pipette assembly and a working area proximate the pipette assembly. The extraction module is movably mounted to the frame and is movable substantially parallel to the horizontal plane at least from an extraction staging area spaced from the pipette assembly and the working area.

In another aspect, there is provided a biologic sample preparation method for use in a system comprising a frame defining a substantially horizontal plane, wherein the frame is divided into three sections, comprising a sample area on the right side of the frame, an extraction staging area on the left side of the frame, and a working area in the middle section of the frame, the method comprising the steps of: moving an extraction module with a pipette tip module under a pipette assembly in a working area; moving the pipette tip assembly downwardly by a controller such that the individual pipettes engage and collect pipette tips on their ends; moving the pipette assembly upwardly away from the pipette tip module; moving an extraction bed on a set of working rails back to the extraction staging area; moving a sampling module on the working rails beneath the pipette assembly in the working area such that predetermined sample containers are positioned under the pipette assembly; moving the pipette assembly vertically toward the appropriate sample containers such that the pipette tips are positioned in the sample containers and the samples are drawn out of the sample containers into the individual pipettes; moving the pipette assembly by the controller away from the sample containers with the samples held in the individual pipettes; moving the sampling module away from the working area and back into the sample area; moving the extraction module from the extraction staging area into the working area such that the extraction station is positioned below the pipette assembly; controlling by the controller the positioning of the pipette assembly over the appropriate tube slots in the extraction plate and the extraction tubes and wherein the reaction mixture with the biological sample therein is transferred from the pipettes into the appropriate extraction tubes and wherein the reaction mixture is retained in the extraction tube by the flow resistant barrier; moving the pipette assembly upwardly out of the appropriate extraction tubes; moving the extraction module on the working rails from the working area back into the extraction staging area; stripping and dropping the tips on the individual pipettes that are contaminated with the biological sample into a waste tips container under the working area, and repeating the above steps until all of the samples are added into the individual extraction tubes of the extraction plate.

In yet another aspect, the preferred present invention is directed to a method of processing a biological sample, comprising applying the biological sample to the sample plate of a biologic sample preparation system according to an embodiment of the invention, and processing the biological sample in the biologic sample preparation system to obtain a processed sample. Preferably, the method further comprises detecting or quantifying a biological molecule in the processed sample. More preferably, the method further comprises detecting or quantifying a nucleic acid (such as chromosomal DNA, plasmid DNA, viral DNA, mRNA, microRNA, a nucleic acid biomarker, etc.) in the processed sample by a PCR processing or a hybridization processing (e.g., using one or more chemiluminescent-labeled nucleic acids), or detecting or quantifying a peptide or protein (such as an antibody, antigen, a protein biomarker, etc.) in the processed sample by an immunoassay, such as radio immuno assay, ELISA, immunofluorescence assay, or chemiluminescence immunoassay.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there is shown in the drawings a preferred embodiment which is presently preferred. It should be understood, however, that the invention is not limited to the precise arrangements and instrumentalities shown. In the drawings:

FIGS. 9A-9E are cross-sectional views of the extraction tube of FIG. 8A taken along line 9-9 of FIG. 8A and related components associated with processing steps of the preparation system of FIG. 2;

FIG. 12 is a top perspective view of a buffer module of the preparation system of FIG. 2;

FIG. 13 is a top perspective view of a buffer container of the buffer module of FIG. 12; and FIG. 13A is a side elevational partial cross-sectional view of the buffer container of FIG. 12, taken along line 13A-13A of FIG. 13.

DETAILED DESCRIPTION OF THE INVENTION

Figure 1:
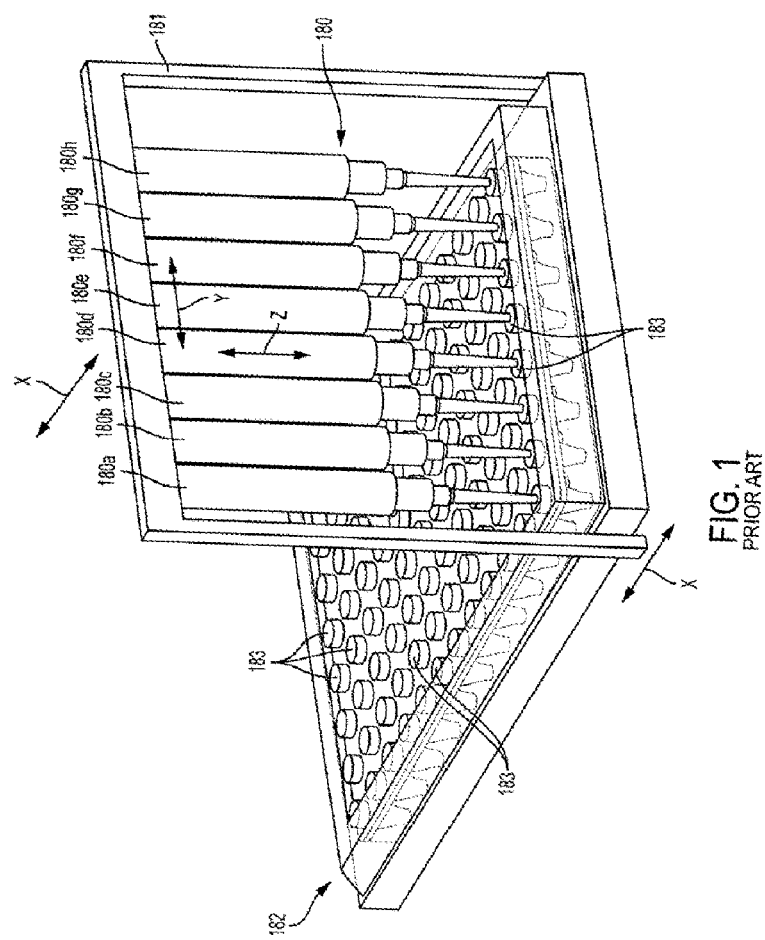
FIG. 1 is a side perspective view of a prior art biologic sample preparation system.

Certain terminology is used in the following description for convenience only and is not limiting. Unless specifically set forth herein, the terms "a", "an" and "the" are not limited to one element but instead should be read as meaning "at least one." The words "right" "left," "lower," and "upper" designate directions in the drawings to which reference is made. The words "inwardly" or "distally" and "outwardly" or "proximally" refer to directions toward and away from, respectively, the geometric center or orientation of the device and instruments and related parts thereof. The terminology includes the above-listed words, derivatives thereof and words of similar import.

It should also be understood that the terms "about", "approximately", "generally," "substantially" and like terms, used herein when referring to a dimension or characteristic of a component of the invention, indicate that the described dimension/characteristic is not a strict boundary or parameter and aid-does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

Figure 2:
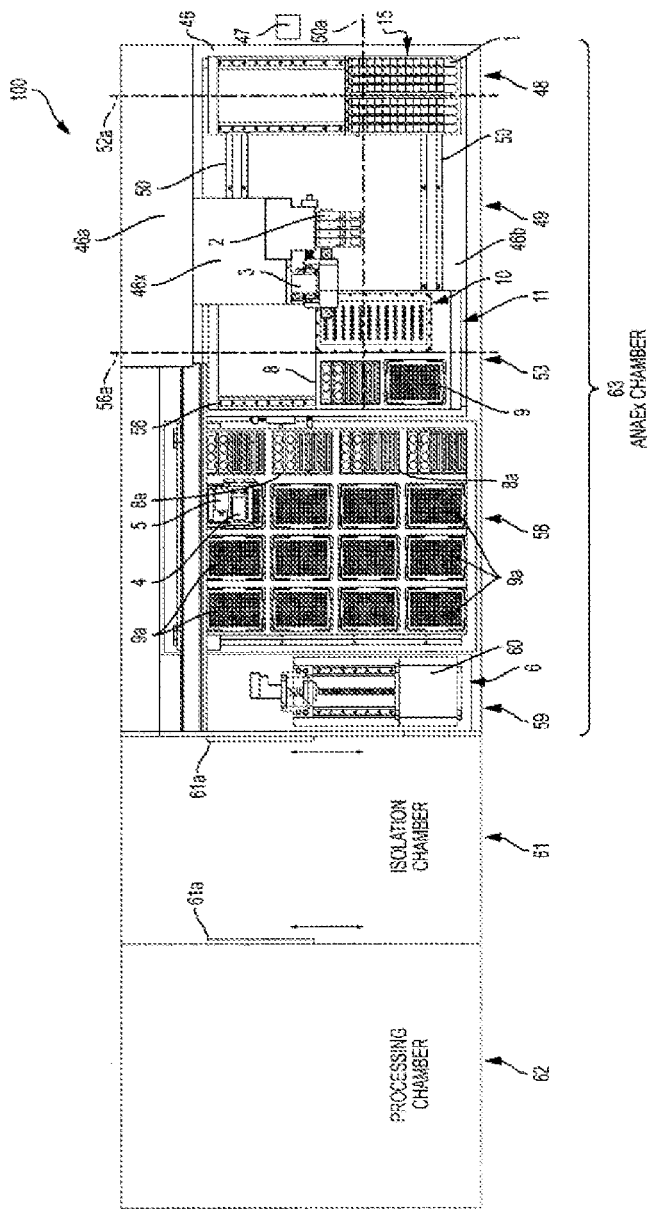
FIG. 2 is a top plain view of a biologic sample preparation system in accordance with a preferred embodiment of the present invention.
Figure 3:
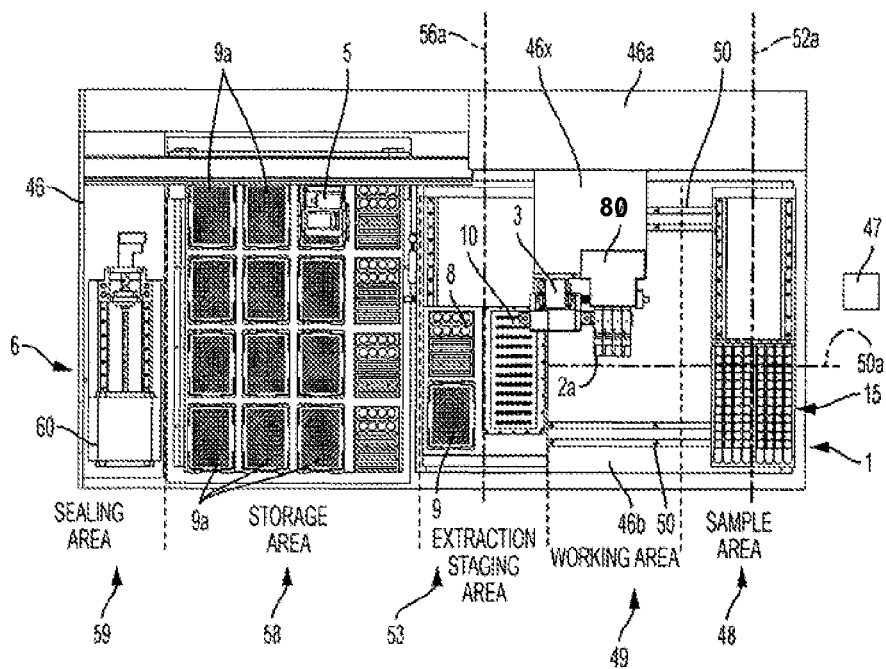
FIG. 3 is a magnified top plan view of a sample area, a working area, an extraction staging area, a storage area and a sealing area of the preparation system of FIG. 2.
Figure 4:
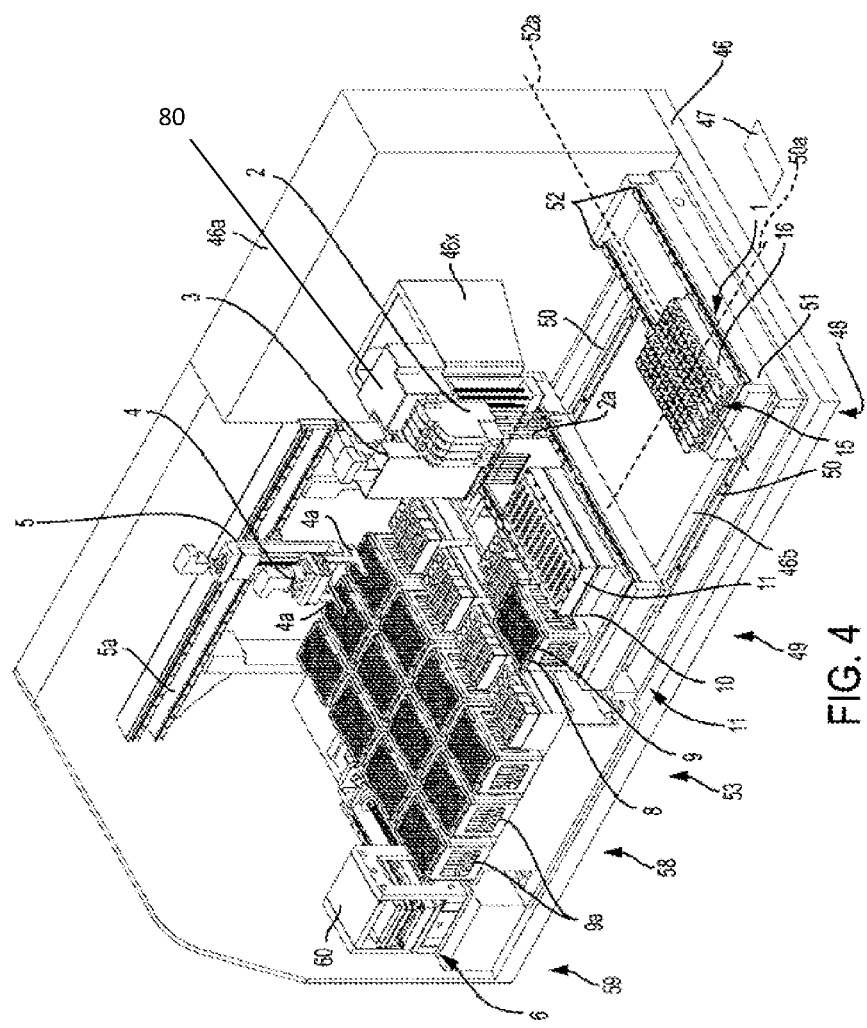
FIG. 4 is a top perspective view of the portions of the preferred preparation system of FIG. 3.

Referring to FIGS. 2-4, the preferred present invention is directed to a biologic sample preparation system, generally designated 100, that prepares biologic samples for analytic processing systems, such as a PCR system, The system 100 includes a frame 46 defining a substantially horizontal plane 47, The frame 46 is preferably constructed of a relatively stiff, strong and sterilizable material that may be assembled to provide structural support to the system 100. The frame 46 may, for example, be constructed of a stainless steel that is biocompatible and sterilizable for use with the system 100. The frame 46 is not limited to being constructed of stainless-steel materials and may be constructed of nearly any relatively strong, stiff material that is able to take on the general size and shape of the frame 46 and withstand the normal operating conditions of the frame 46.

The frame 46 preferably defines the horizontal plane 47 that is generally, but not necessarily, oriented substantially horizontal relative to a ground surface (not shown) associated with the system 100. The horizontal plane 47 is preferably substantially horizontal such that fluid materials utilized with the system 100 are maintained in their associated containers during manufacturing, as will be described in greater detail below. The horizontal plane 47 is not referenced from specific portions of the frame 46, but is generally defined by the frame 46 and the associated components that are positioned on and supported by the frame 46, particularly the components that are movable on the frame 46, as is described in greater detail below.

The preferred sample preparation system 100 includes a pipette assembly 2 including a first pipette 2a, a second pipette 2b, a third pipette 2c and a fourth pipette 2d in the preferred embodiment. The pipette assembly 2 is movably mounted to the frame 46. The frame 46 of the preferred embodiment includes a vertical support 46a with a pipette support bracket 46x extending therefrom. The vertical support 46a and the pipette support bracket 46x support the movable pipette assembly 2 above a frame table 46b of the frame 46. The pipette assembly 2 is movable in the preferred embodiment only in a direction substantially perpendicular to the horizontal plane 47 or substantially vertically during operation. The pipette assembly 2 is specifically movable vertically in the preferred embodiment on the pipette support bracket 46x to limit the movement of the pipette assembly 2 to substantially vertical movements or to movements generally perpendicular to the horizontal plane 47. This limited substantially vertical movement of the pipette assembly 2 simplifies the movements of the pipette assembly 2 and substantially eliminates horizontal stopping and starting movements of the pipette assembly 2, which are common in prior art systems and result in potential contamination of samples. In the preferred embodiment, the pipette assembly 2 has no horizontal movement to reduce the potential for contamination of samples if the pipette assembly 2 were moved both horizontally and vertically, thereby creating potential for shaking contamination droplets from the pipette assembly 2 or creating airborne potentially contaminating materials during these movements.

The first, second, third and fourth pipettes 2a, 2b, 2c and 2d of the preferred pipette assembly 2 are utilized to move samples during the sample preparation process, as would be understood by one having ordinary skill in the art. The sample preparation system 100 is not limited to including the first, second, third and fourth pipettes 2a, 2b, 2c, 2d and may function utilizing only the first pipette 2a or may include more than the four preferred pipettes 2a, 2b, 2c, 2d described herein, such as including eight (8) pipettes that is adapted for use with an eight by twelve (8×12) well base, as would be understood by one having ordinary skill in the art, or more pipettes. The pipette assembly 2 and functioning of the pipettes 2a, 2b, 2c, 2d is preferably remotely controlled by a. controller 80 during operation of the sample preparation system 100.

Referring to FIGS. 2-5, the biologic sample preparation system 100 also includes a sample module 1 having a sample plate 16. The sample module 1 is movably mounted to the frame 46 and, specifically, to the frame table 46b in the preferred embodiment. The sample module 1 is movable substantially parallel to the horizontal plane 47 at least from a sample area 48 spaced from the pipette assembly and a working area 49 proximate the pipette assembly 2. The preferred sample module 1 is mounted on working rails 50 that are attached to the frame table 46b. The preferred working rails 50 extend from the sample area 48, across the working area 49 and into an extraction staging area 53. The working rails 50 preferably permit lateral, movement of the sample module 1 on the frame table 46. The movement is preferably limited to substantially linear movement of the sample module 1 on the frame or working rails 50. The sample module 1 is not limited to being mounted on the working rails 50 on the frame table 46b and may be alternatively, movably mounted to the frame 46 for movement between the sample area 48 and working area 49, such as by a robotic arm or other movement mechanism.

In the preferred embodiment, the sample module 1 includes a sample bed 51 having sample rails 52 mounted thereon, sample holders 15 and sample containers 14 mounted to the sample plate 16. The sample plate 16 is preferably movably mounted on. sample rails 52 such that the sample plate 16 is moveable relative to the frame 46 substantially parallel to a sample rail axis 52a. A sample rail axis 52a is positioned substantially parallel to the horizontal plane 47.

The sample plate 16 is preferably, movably mounted to the sample bed 51 on sample rails 52 for movement in a substantially linear direction parallel to the sample rail axis 52. The sample plate 16 is not limited to being mounted to the sample bed 51 on the example rails 52 and may be alternatively mounted to the sample bed 51 by other mechanisms such as driven ropes and pulleys, robotic arms or other mechanisms that permit movement of the sample plate 16 relative to the sample bed 51. The sample holders 15 of the preferred embodiment are preferably comprised of eight (8) sample holders 15a, 15b, 15c, 15d, 15e, 15f, 15g, 15h arranged in rows substantially parallel to the sample rail axis 52a that are individually movable relative to the sample plate 16. Each of the sample holder rows 15a-15h include at least one and preferably twelve (12) sample containers 14 mounted thereto. The sample preparation system 100 is not limited to including the eight (8) sample holders 15a-15h arranged in rows having twelve (12) sample containers 14 in each row and may include only a single sample holder 15 with a single sample container 14 mounted thereto or may include more or less sample holders 15a-15h and containers 14 than is shown in the preferred embodiment. The system 100 may also be configured for operation with two (2) or eight (8) sample holders 15a-15h or three hundred eighty-four (384) sample holders 15a-15h, which may be configured as four (4) sample modules 1 having ninety-six (96) samples aligned simultaneously. The eight (8) sample holders 15a-15h with twelve (12) sample containers 14 associated with each is, however, preferred resulting in ninety-six (96) samples associated with the sampling module 1.

Figure 5:
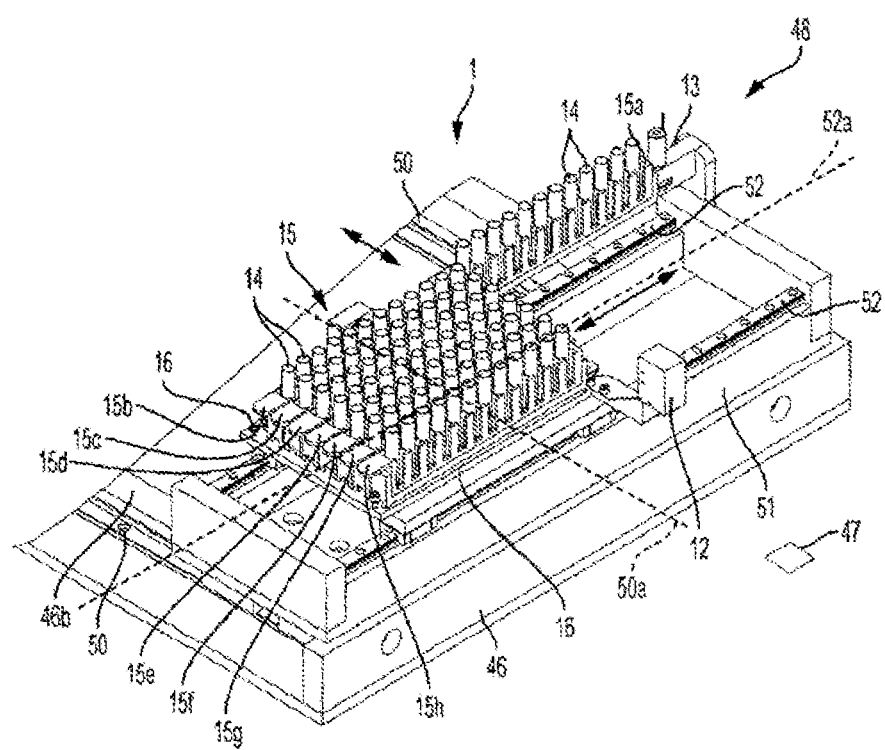
FIG. 5 is a magnified top perspective view of the sample area and related components of the preparation system of FIG. 3.

Each of the preferred sample holders 15a-15h are preferably moveable parallel to the sample rail axis 52a during use for scanning and identifying the individual sample containers 14 during processing. As is shown in FIG. 5, for example, the first sample holder row 15a may move relative to the sample table 16 generally linearly and parallel to the sample rail axis 52a to extend the first sample holder 15a away from the remaining sample holders 15b-15h, which are positioned on the sample plate 16. The sample module 1 preferably includes a bar code scanner 12 mounted to the sample plate 16 and an electromagnetic lock 13 mounted to the sample bed 51. When the first sample holder 15a moves away from the remaining sample holders 15b-15h, the bar code scanner 12 scans the individual sample containers 14 for identification purposes. The electromagnetic lock 13 locks the first sample holder 15a in an extended position when the first sample holder 15a is fully extended. The bar code scanner 12 reads bar codes on the sample containers 14 mounted in the first sample holder 15a as the first sample holder 15a is extended to the fully extended position by moving toward the vertical support 46a substantially parallel to the sample rail axis 52a. The remaining second through eighth sample holders 15b-15h are similarly extended and scanned by the bar code scanner 12 and secured by the electromagnetic lock 13, respectively.

The sample plate 16 with the attached sample holders 15 and sample containers 14 are able to move relative to the frame 46 and, specifically, relative to the sample bed 51 and the frame table 46b by movement along the sample rails 52 toward or away from the vertical support 46a. This movement of the sample plate 16 is preferably, substantially parallel to the horizontal plane 47 and to the sample rail axis 52a. The sample holders 15, sample containers 14 and sample bed 51 are all preferably movable on the working rails 50 in front of the vertical support 46a. This movement of the sample bed 51 is preferably parallel to the horizontal plane 47 and a working rail axis 50a defined by the working rails 50. These movements permit positioning of the sample containers 14 in multiple, and varied positions in the sample area 48 and the working area 49 during operation as will be described in greater detail below.

Referring to FIGS. 2, 3, 7A and 7B, the sample preparation system 100 also includes an extraction module 11 including an extraction plate 20. The extraction module 11 is, movably mounted to the frame 47. The extraction module 11 is movable substantially parallel to the horizontal plane 47 at least from an extraction staging area 15 spaced from the pipette assembly 2 and the working area 49 proximate the pipette assembly 2.

In the preferred embodiment, the working rails 50 are mounted substantially parallel to the horizontal plane 47 on the frame 46. The working rails 50 define the working rail axis 50a that is oriented substantially parallel to the horizontal plane 47 and perpendicular to the sample rail axis 52a in the preferred embodiment. The working rails 50 extend across the working area 49 and into the extraction stage area 53 and the sample area 48.

Figure 7A:
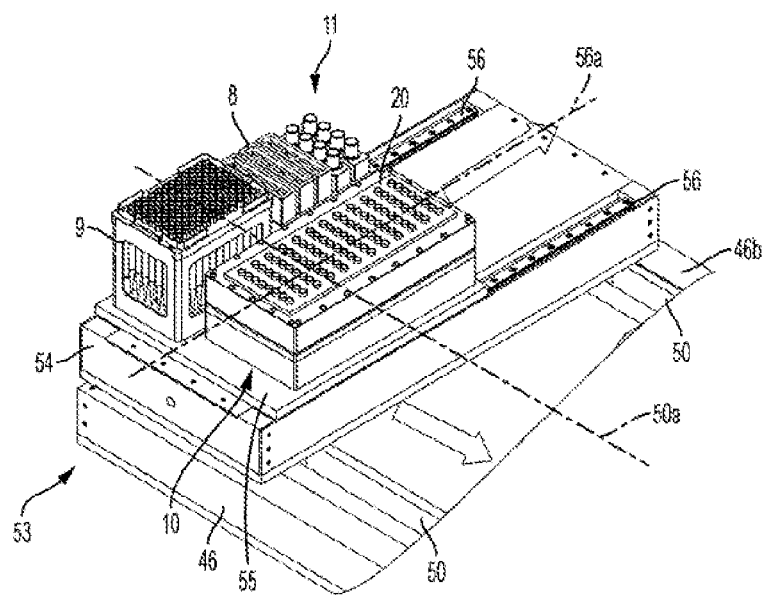
FIG. 7A is a top perspective view of the extraction staging area and related components of the preparation system of FIG. 3.
Figure 7B:
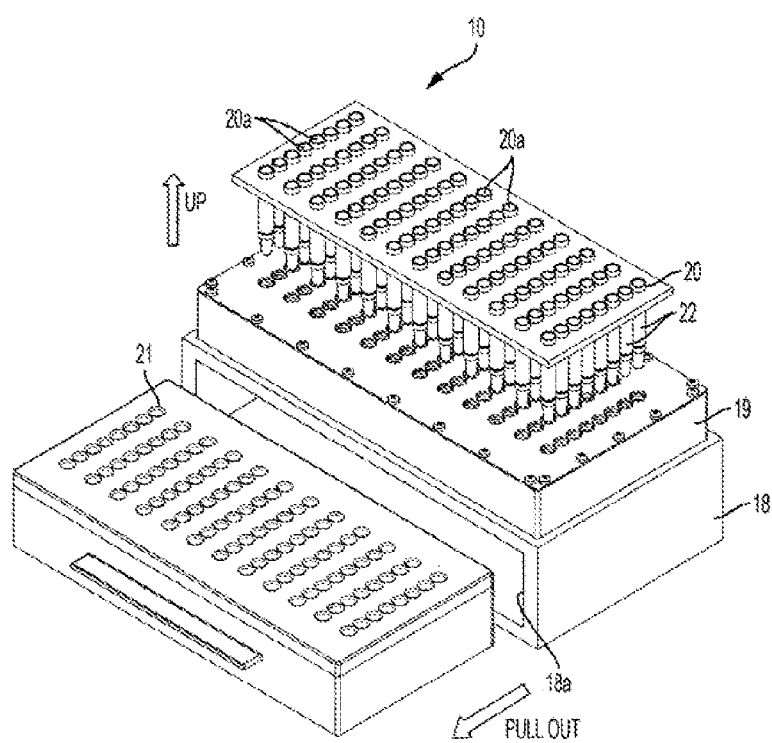
FIG. 7B is a partially exploded top perspective view of an extraction module of the preparation system of FIG. 2.

Referring to FIGS. 7A and 7B, the extraction module 11 preferably includes an extraction bed 54 mounted to the working rails 50 and an extraction support 55 movably mounted on the extraction bed 54. The extraction module 11 also preferably includes an extraction station 10, a pipette tip module 9 and a buffer module 8. The extraction support 55 is movably mounted on extraction rails 56 such that the extraction support 55 is movable relative to the frame 46 parallel to an extraction rail axis 56a. The extraction rail axis 56a is positioned substantially parallel to the horizontal plane 47 and to the sample rail axis 52a.

The working rails 50 define the working rail axis 50a and extend across the working area 49 and into the extraction staging area 53 and the sample area 48. The working rail axis 50a is positioned substantially perpendicular relative to the extraction rail axis 50a and substantially parallel to the horizontal plane 47. The extraction bed 54 is movably mounted to the working rails 50 and the extraction support 55 is movably mounted to the extraction bed 54 on the extraction rails 56. Accordingly, the extraction bed 54 and extraction support 55 are respectively movable on the frame 46 along the working and extraction rails 50, 56 to selectively position the extraction station 10, buffer module 8 and pipette tip module 9 at various locations in the extraction staging area 53 and the working area 49.

Movement of the extraction module 11 and its various components in the working area 49 and extraction staging area 53 along the working rails 50 and the extraction rails 56 is substantially linear along the individual working and extraction rails 50, 56, respectively, to substantially control the movements of the extraction bed 54 and related components of the extraction module 11. These substantially linear movements are comparatively simple relative to traditional robotic and three dimensional movements associated with PCR systems.

The movement of the extraction bed 54 on the working rails 50 and the extraction support 55 on the extraction rails 56 is preferably controlled remotely by a controller 80. The movements are not limited to being remotely controlled by a controller and may be manually controlled by a user or mechanically controlled without the controller. The controller is, however, preferred for coordinating precise movements of the extraction bed 54 and extraction support 55 on the working and extraction rails 50, 56, respectively. In addition, utilization of the controller is also preferred to control movement of the sample bed 51 and extraction bed 54 on the working rails 50 to prevent interference in the movements between the sample bed 51 and extraction bed 54 and for coordinated movements during processing, as is described in greater detail below.

In the preferred embodiment the extraction rails 56 define the extraction rail axis 56a and the working rails 50 define the working rail axis 50a. The working rail axis 50a is positioned substantially perpendicular relative to the extraction rail axis 56a and substantially parallel relative to the horizontal frame 47. The extraction bed 54 is movably mounted to the working rails 50.

The extraction station 10, the pipette tip module 9 and buffer module 8 are preferably mounted to the extraction support 55. Accordingly, when the extraction support 55 moves on the extraction rails 56, the extraction station 10, the pipette module 9 and the buffer module 8 move relative to the frame 46 and the extraction bed 54. The PCR system 100 is not limited to having this particular arrangement for movement of the buffer module 8, the pipette module 9 and the extraction station 10, which may be otherwise mounted to the frame 46 for movement thereto.

Referring to FIGS. 7B-10, the extraction station 10 preferably includes a waste housing 18, a waste tank 21, a magnet and heat module 19 and an extraction plate 20. The magnet and heat module 19 preferably includes upper and lower core plates 31, a heating plate 33, a plurality of heating rods 34 and a plurality of electromagnetic coils 35. The core plates 31 include a plurality of tube holes 31a therein. A plurality of extraction tubes 22 are mounted in the plurality of tube holes 31 in an assembled configuration. The waste housing 18 and waste tank 21 are preferably constructed of a structural, biocompatible and autoclavable material, such as stainless steel, but are not so limited and may be constructed of any material that is able to take on the general size and shape of the waste housing 18 and the waste tank 21 and withstand the normal operating conditions of the waste housing 18 and the waste tank 21. In the preferred configuration, the waste tank 21 is removably mountable in a tank slot 18*a* of the waste housing 18. The waste tank 21 is preferably slidably and removably mountable in the waste housing 18 by slidable insertion into and out of the tank slot 18*a*. The waste housing 18 is not limited to including the tank slot 18*a* and the shown and described removable mounting of waste tank 21, but this configuration is preferred for removal and disposal of waste that accumulates in the waste tank 21.

The extraction plate 20 preferably includes tube slots 20*a* therein that accommodate extraction tubes 22 and support the extraction tubes 22 and assembled configuration. The extraction plate 20 preferably includes ninety-six (96) tube slots 20*a* arranged in an eight by twelve (8×12) matrix corresponding to the sample containers 14 of the sample holders 15. The extraction plate 20 is not limited to including the preferred ninety-six (96) tube slots 20*a* and may include a single tube slot 20*a* to accommodate a single extraction tube 20 or may include more than ninety-six (96) tube slots 20*a*, such as the above-described three hundred eighty-four (384) tube slots 20*a*, to accommodate additional extraction tubes 22.

Figure 10:
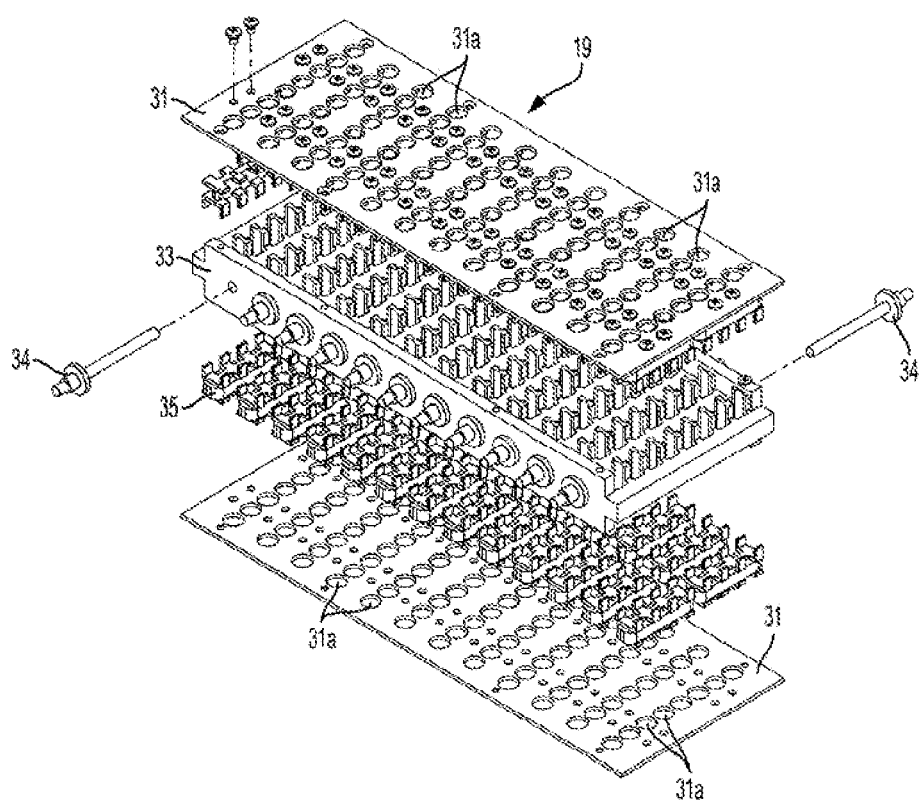
FIG. 10 is an exploded, top perspective view of a magnet and heating module of the preparation system of FIG. 2.

Referring to FIG. 10 in the preferred embodiment, the magnet and heat module 19 includes the core plates 31, the heating plate 33, the plurality of heating rods 34 and the plurality of magnetic coils 35. The core plates 31 include the plurality of tube holes 31*a* therein that are preferably configured in the same eight by twelve (8×12) matrix as the preferred tube slots 20 and sample containers 14 of the extraction station 10. Similarly, the core plates 31 are not limited to each including the ninety-six tube hales 31*a* and may include a single tube hole 31*a*, a pair of tube holes 31*a* or additional tube holes 31*a* in excess of the preferred ninety-six (96) to accommodate a single extraction tube 22 or nearly any number of additional extraction tubes 22, respectively. In an assembled configuration, the plurality of extraction tubes 22 is mounted in the plurality of tube holes 31*a* and in the tube slots 20*a*. The electromagnetic coils 35 are configured to apply a magnetic field to the individual extraction tubes 22 during use and the heating plate 33 and plurality of heating routes 34 are configured to heat the extraction tubes 22 and the materials therein to a predetermined temperature for processing.

Figures 8A, 8B, 8C:
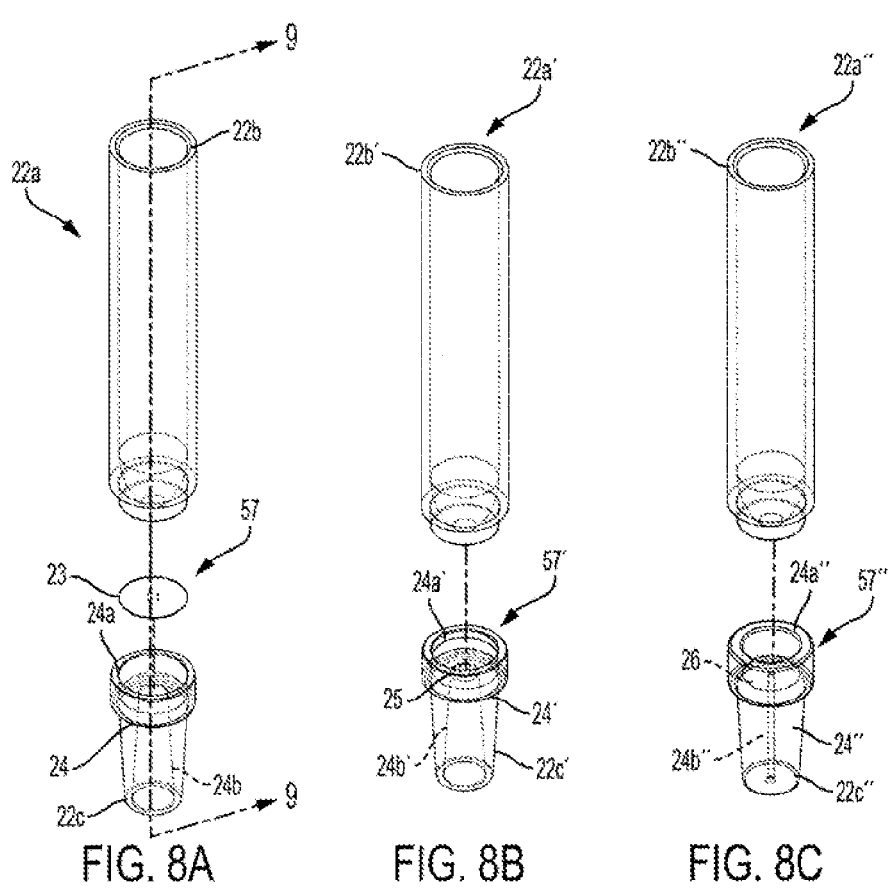
FIG. 8A is a front perspective view of a first preferred extraction tube of the preparation system of FIG. 2.
FIG. 8B is a front perspective view of a second preferred extraction tube of the preparation system of FIG. 2.
FIG. 8C is a front perspective view of a third preferred extraction tube of the preparation system of FIG. 2.

Referring to FIGS. 8A-8C, first, second and third preferred embodiments of a first extraction tube 22*a*, 22*a*', 22*a*" of the plurality of extraction tubes 22 are utilized with the PCR system 100. The first extraction tube 22*a*, 22*a*', 22*a*" of the preferred embodiments is representative of the individual plurality of extraction tubes 22 and the details of the plurality of extraction tubes 22 are described by the first extraction tube 22*a*, 22*a*', 22*a*". The first, second and third preferred first extraction tubes 22*a*, 22*a*', 22*a*" include similar features and similar references numbers are utilized herein to identify those similar features with a prime symbol (') utilized to distinguish the first extraction tube 22*a*' of the second preferred embodiment and a double prime symbol (") utilized to distinguish the first extraction tube 22*a*" of the third preferred embodiment The first extraction tube 22*a*, 22*a*', 22*a*" of the first, second and third embodiments includes a top end 22*b*, 22*b*', 22*b*" and a bottom end 22*c*, 22*c*', 22*c*". A flow resistant barrier 57, 57', 57" is positioned in the first extraction tube 22*a*, 22*a*' 22*a*" proximate the bottom end 22*c*.

Referring to FIG. 8A, in the first preferred embodiment, the first extraction tube 22*a* is configured such that a top portion associated with the top tube end 22*b* is separately formed and attachable from a bottom portion associated with the bottom tube end 22*c*. The bottom tube end 22*c* is associated with a vent tube 24 with an upper cup-shaped portion 24*a* and an outwardly tapering slot 24*b* adjacent the bottom tube end 22*c*. In the first preferred embodiment, the cup-shaped portion 24*a* is configured to receive a punctured polymeric film 23 that is secured and sandwiched between the upper lower portions of the first extraction tube 22*a* in an assembled configuration. The punctured polymeric film 23 is configured to prevent flow of a reaction mixture 27 through the bottom tube end 22*c* under a pressure less than or equal to atmospheric pressure. Accordingly, when reaction mixture 27 is positioned in the upper portion of the first extraction tube 22*a*, the punctured polymeric film 23 prevents the reaction mixture 27 from flowing out of the outwardly tapering slot 24*b* and out of the first extraction tube 22*a* under atmospheric pressure. Applying additional pressure above atmospheric pressure to the top of the reaction mixture 27 permits flow of the reaction mixture 27 through the punctured polymeric film 23 and out of the outwardly tapering slot 24*b*. The punctured polymeric film 23 mounted between the upper and lower portions of the first extraction tube 22*a* defines the flow resistant barrier 57 of the first preferred embodiment. This flow resistant barrier 57 retains fluid in the first extraction tube 22*a*, particularly waste liquid 28, but also permits flow of the waste liquid 28 therethrough when appropriate force is applied to the waste liquid 28. The waste liquid 28, therefore, flows in through the top tube end 22*b* and out of the bottom tube end 22*c*, eliminating the need to remove the waste liquid 28 out of the top tube end 22*b* and potential contamination of adjacent samples that may result from such extraction of the waste liquid 28. The punctured polymeric film 23 may be constructed of nearly any material that is able to take on the size and shape of the punctured polymeric film 23, withstand the normal operating conditions of the punctured polymeric film 23 and perform the preferred functions of the punctured polymeric film 23. The punctured polymeric film 23 may be constructed of a latex material, a rubber material or another similar material.

Referring to FIG. 8B, in the second preferred embodiment, the first extraction tube 22*a*' includes the vent tube 24 with a microhole 25 integrally formed in the vent tube 24 at a center in the bottom of the upper cup-shaped portion 24*a*', The microhole 25 and vent tube 24' of the second preferred embodiment are designed and configured to prevent the reaction mixture 27 from flowing through the flow resistant barrier 57 under pressure at and less than atmospheric pressure and to permit flow of the waste liquid 28 through the outwardly tapering slot 24*b*' when greater pressures are applied to the top of the waste liquid 28.

Referring to FIG. 8C in the third preferred embodiment of the first extraction tube 22*a*", the flow resistant barrier 57" is comprised of a capillary 26 integrally formed in the vent tube 24" at the bottom tube end 22*c*". The capillary 26 is similarly designed and configured to prevent flow of the reaction mixture 27 through the capillary 26 when the reaction mixture 27 is subjected to atmospheric or less pressure and to permit flow of the waste liquid 28 through the capillary 26 when subjected to a predetermined pressure greater than atmospheric pressure.

Referring to 8A-8C, the first extraction rube 22a, 22a', 22a" of the preferred embodiments is not limited to a two-piece construction and may be constructed and integrally formed as a one-piece component or may be assembled from various additional components. The first extraction tube 22a, 22a', 22a" is preferably constructed of a biocompatible, sterilizable material that is able to take on the general size and shape of the first extraction tube 22a, 22a', 22a" and withstand the normal operating conditions of the first extraction tube 22a, 22a', 22a".

Referring to FIGS. 2-4, the sample preparation system 100 preferably includes a storage area 58 adjacent the extraction staging area 53 that is supported by the frame 46. The storage area 58 preferably includes a plurality of storage pipette tip modules 9a therein that are also supported by the frame 46.

The preferred sample preparation system 100 includes a storage area robotic system 5 having a gripper 4 mounted to the vertical support 46a adjacent the pipette assembly 2. The storage area robotic system 5 is preferably movably mounted to a robot rail 5a that is secured to the vertical support 46a for movement relative to the frame 46 in the extraction staging area 53, the storage area 58 and the sealing area 59. The gripper 4 preferably includes arms 4a extending downwardly therefrom that are movable to releasably grasp and release buffer modules 8, storage pipette tip modules 9a and pipette tip modules 9 for moving these and other components to and between the extraction staging area 53, the storage area 58 and the sealing area 59. The sample preparation system 100 is not limited to including the robotic system 5 with the gripper 4 for moving and manipulating the buffer, storage pipette tip and pipette tip modules 8, 9a, 9 and these components may be manually moved or may be moved by alternative mechanisms or systems for desired placement of the components on the biologic sample preparation system 100.

A heat sealing module 6 is preferably positioned in the sealing area 59. The heat sealing module 6 is preferably supported by the frame 46 and is adjacent the storage area 58. Following extraction and amplification of the nucleic acid, the amplified samples are sealed in the heat sealing module 6 by a sealing mechanism 60 for storage or shipping. Accordingly, in the preferred embodiment, the sample preparation system 100 includes the sample area 48, the working area 49, the extraction staging area 53, the storage area 58 and the sealing area 59, which are each supported by the same frame 46 having a single footprint as opposed to being located in various rooms or areas. Consolidation of each of these areas on the frame 46 reduces the footprint of the sample preparation system 100 and reduces the need to transport associated components over relatively large distances, resulting in potential contamination and delay in the processing.

Referring to FIGS. 7B and 9B-9D, in the preferred embodiment magnetic beads 29 and a reaction mixture 27 are positioned in the extraction tubes 22 during a portion of the processing using the preferred sample preparation system 100. The extraction tube 22 shown in FIGS. 9A-9E is a generic extraction tube 22, which may be comprised of any of the first, second or third preferred first extraction tubes 22a, 22a', 22a" described above and shown in FIGS. 7A-7C, respectively. When the extraction tubes 22 are positioned in the tube slots 20a of the extraction plate 20 in the extraction station 10, electromagnets 30 are positioned adjacent the sides of the extraction tubes 22 proximate their bottom tube ends 22c. When the electromagnets 30 associated with the electromagnetic coils 35, are powered, a magnetic field is created that draws the magnetic beads 29 toward edges or inner side surfaces of the extraction tubes 22 proximate the electromagnets 30. This process is utilized to amplify nucleic acid, as is described in greater detail below. This utilization of the magnetic beads 29 and the electromagnets 30 also eliminates the need for a shaker unit, which is used in prior art systems and creates the potential for creation of contaminating droplets or airborne particles.

Figure 11:
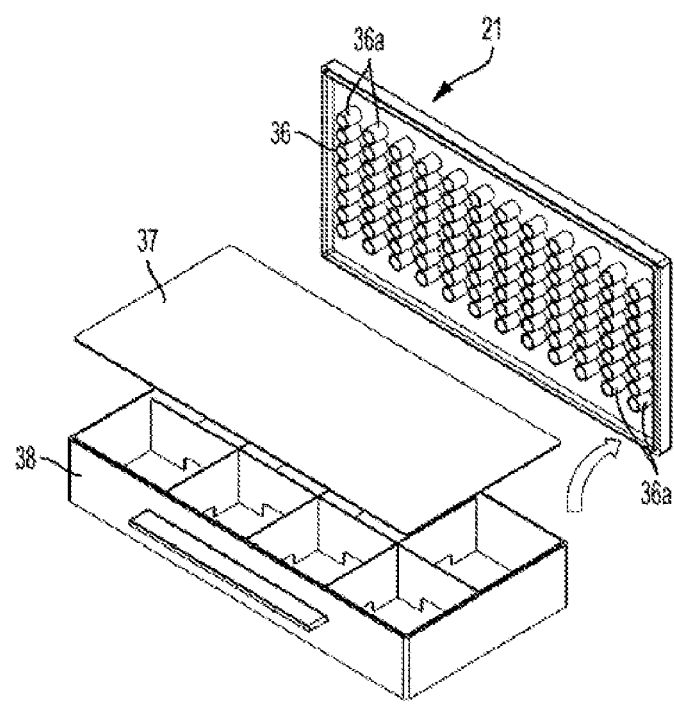
FIG. 11 is a partially exploded, top perspective view of a waste tank of the preparation system of FIG. 2.

Referring to FIGS. 7B and 11, the waste tank 21 of the sample preparation system 100 preferably includes a waste liquid tank cover 36, a drainage part, 37 and a waste liquid basin 38. The waste liquid tank cover 36, drainage parts 37 and waste liquid basin 38 are preferably constructed of structural materials that are able to take on the general size and shape of these components and withstand the normal operating conditions of the components. The components are also preferably construction of materials that may be sterilized. The waste liquid tank cover 36 preferably includes waste liquid holes 36a in an eight by twelve (8×12) matrix arrangement that corresponds with the tube holes 31a and tube slots 20a, but are similarly not limited to this configuration. The waste liquid holes 36a permit waste 28 to flow past the waste liquid tank cover 36, through the drainage parts 37 and into the waste liquid basin 38 for disposal.

Referring to FIGS. 2, 7A and 12-13A, the preferred biologic sample preparation system 100 includes the buffer modules 8 that are typically positioned in the extraction staging area 53 on the extraction station 10. The preferred sample preparation system 100 also preferably includes storage buffer modules 8a that are positioned in the storage area 58 for transfer to the extraction station 10. The buffer modules 8 and storage buffer modules 8a are substantially the same structurally. The buffer module 8 preferably includes a buffer housing 42, buffer containers 39 removably mountable in the buffer housing 42, cartridge containers 41 removably mountable in the buffer housing 42 and cartridges 40 removably mountable in the cartridge containers 41. The preferred buffer containers 39 include buffer grooves 43b on lower outer surfaces and a splash cover 44 removably mountable to an open upper end. The buffer housing 42 includes internal housing grooves 42a. The cartridge containers 41 include external cartridge grooves 43a on outer surfaces and cartridge holes 41-a in an upper surface that support the cartridges 41 therein with an upper portion of the cartridges 40 extending out of the cartridge containers 41. The housing grooves 42a are designed and configured to mate with the cartridge grooves 43a and buffer grooves 43b such that the buffer containers 39 and cartridge containers 41 may only be positioned in predetermined and particular locations in the buffer housing 42. Proper positioning of the buffer container 39 and cartridge containers 41 in the buffer housing 42 ensures the controller appropriately manipulates the buffer module 8 during use as is described in greater detail below. The buffer container 39 also preferably includes internal splash prevention ends 45.

Referring to FIGS. 3, 4 and 6A-6F, an aeration pipetter module 3 is preferably mounted to the vertical support 46a of the frame 46 for substantially vertical movement or movements substantially perpendicular relative to the horizontal plane 47. In the preferred embodiment, the aeration pipetter module 3 is secured to and moves with the pipette assembly 2. The aeration pipetter module 3 is not limited to being mounted to the pipette assembly 2 and may be separately mounted or otherwise configured to interact with the extraction station 10, as will be described in greater detail below. For example, the aeration pipetter module 3 may be pivotably mounted to the frame 46 or may be configured for arcuate movement relevant to the frame 46 to positions spaced above and adjacent the extraction station 10.

Referring to FIG. 2, the preferred biologic sample preparation system 100 also includes an isolation chamber 61 having isolation doors 61a and a processing chamber 62, which may be comprised of a qualitative PCR ("qPCR") chamber when the samples are being prepared for a PCR system, positioned adjacent the isolation chamber 61. The isolation chamber 61 and processing chamber 62 are both preferably supported by the frame 46. The isolation doors 61 are preferably slidably mounted to the frame 46 to selectively open and close the isolation chamber 61. The isolation chamber 61 is preferably positioned immediately adjacent the sealing area 59 on one side with the processing chamber 62 positioned on the opposite side of the isolation chamber 61. This preferred sample preparation system 100, therefore, includes the sample area 48, the working area 49, the extraction staging area 53, the storage area 58, the sealing area 59, the isolation chamber 61 and the processing chamber 62 in a single footprint supported by the frame 46. The single footprint consolidates the sample preparation system 100, wherein prior art systems required multiple rooms that were spaced apart from each other to accommodate each of these areas of the PCR process. The consolidated footprint reduces potential contamination of the samples and creates efficiency in the preferred sample preparation system 100.

In the preferred biologic sample preparation system 100, the various areas can also be broken down into an automatic nucleic acid extractor "ANAEx" chamber 63, the isolation chamber 61 and the qPCR chamber 62. The ANAEx chamber 63 preferably includes the sample area 48, the working area 49, the extraction staging area 53, the storage area 58 and the sealing area 59. Each of these areas is mounted on the frame 46 in a single footprint, thereby reducing the footprint compared to prior art systems, which required multiple rooms and significant spacing between these areas.

Referring to FIGS. 2-5, in operation, the preferred sample preparation system 100 is set up for operation by positioning the sampling module 1 in the sample area 48. Individual sample containers 14 are loaded with biological materials, such as whole blood, serum, or other biological materials for nucleic acid amplification. The sample containers 14 are positioned in the sample holders 15, preferably in the described eight by twelve (8×12) matrix arrangement. The sample containers 14 each preferably contain a bar code mounted thereon. The sample bed 51 is moved to the end of the frame 46 into the working area 48 (FIG. 4) and the array of sample containers 14 and sample holders 15 are positioned in a front portion of the working area 48 on the sample bed 51 (FIG. 4). The first sample holder 15a is moved rearwardly toward the vertical support 46a such that the bar code scanner 12 is able to scan the bar codes on the sample containers 14 on the first sample holder 15a and communicate the identification information, to the controller. The first sample holder 15a is moved by the controller back into alignment with the remaining sample holders 15a-15h. The sample bed 51 then moves laterally on the working rails 50 toward the working area 49 to align the second sample holder 15b with the electromagnet lock 13. When aligned, the second sample holder 15b is moved by the controller rearwardly toward the vertical support 46a and the electromagnetic lock 13 such that the bar codes on the sample containers 14 in the second sample holder 15b can be read by the bar code scanner 12. In the fully extended position, the second sample holder 15b is locked into position by the electromagnetic lock 13. This process is repeated until each of the bar codes on each of the sample containers 14 are examined by the bar code scanner 12 and the identification information is communicated to the controller.

Referring to FIGS. 2-4, 7A and 7B, the extraction module 11 is preferably configured with the extraction station 10 mounted to the extraction support 55 in a front corner, a pipette tip module 9 mounted proximate the extraction station 10 on the extraction support 55 and the buffer module 8 mounted to a rear corner of the extraction support 55 relative to the pipette tip module 9. The extraction bed 54 is preferably position by the controller in the extraction staging area 53.

The pipette assembly 2 and the aeration pipetter module 3 are preferably oriented and position above the working area 49 such that aeration tips 3a and tips of the individual pipettes 2a, 2b, 2c, 2d are positioned above upper surfaces of the sample containers 14, extraction tubes 22 and other components of the extraction module 11 and sampling module 1 and spaced therefrom.

The storage area 58 is preferably configured to include multiple storage buffer modules 8a and storage pipette tip modules 9a that may be manipulated by the storage area robotic system 5 for replacement of the buffer module 8 and pipette tip module 9 on the extraction module 11.

Referring to FIGS. 2-7B, the preferred sample preparation system 100 is designed for one-directional flow of liquids involved in the process. In addition, the preferred sample preparation system 100 is configured for mechanical movements that involve substantially linear movement of the components during use pf the system. This one-directional flow and linear movement of the components is designed to reduce or eliminate possible causes of cross-contamination that exist in prior art sample preparation systems. For example, the pipette assembly 2 and aeration pipetter module 3 are mounted to the vertical support 46a and pipette support bracket 46x for substantially vertical movement perpendicular to the horizontal plan 47. In addition, the sample bed 51 and extraction bed 54 are configured for substantially linear movement along the working rails 50 for movement between the sample area 48, the working area 49 and the extraction staging area 53, respectively. Further, the extraction support 55 is configured for substantially linear movement on the extraction rails 56 and the sample plate 16 is configured for substantially linear movement on the sample rails 52. The individual sample holders 15a-15h is also configured for one-dimensional or linear movement relative to the sample plate 16 for reading of the bar codes by the bar code scanner 12. Each of these one-directional or linear movements reduce or eliminate potential causes of cross contamination and work with gravitational force to retain the fluids in the extraction tubes 22 associated with the preferred biologic sample preparation system 100.

Figure 6A:
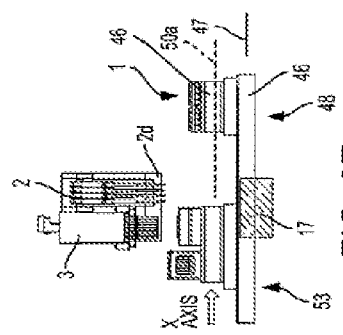
FIGS. 6A-6F are a series of front elevational views showing movement of components of the preferred preparation system in the extraction staging area, the working area and the sample area of the preferred preparation system of FIG. 3.
Figure 6B:
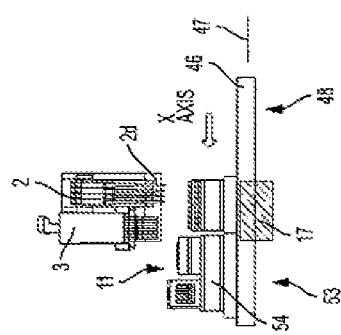
Figure 6C:
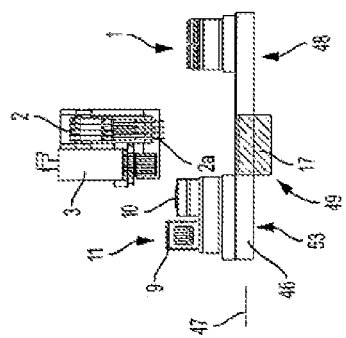
Figure 6D:
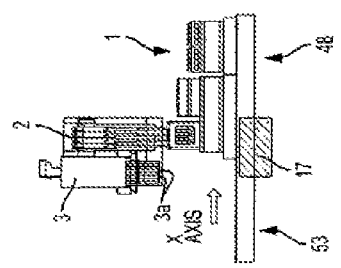
Figure 6E:
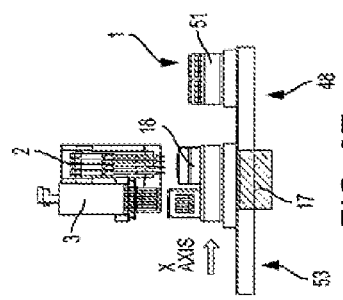
Figure 6F:
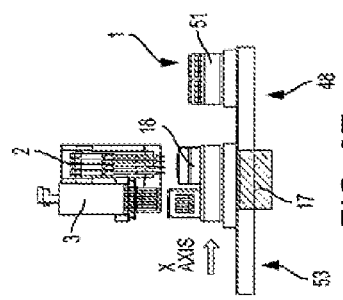

In operation, following scanning of the sample containers 14, the pipette tip module 9 is moved under the pipette assembly 2 in the working area 49. The pipette tip assembly 2 is moved downwardly by the controller such that the individual pipettes 2a, 2b, 2c, 2d engage and collect pipette tips on their ends. The pipette assembly 2 is then moved upwardly away from the pipette tip module 9 and the extraction bed 54 is moved on the working rails 50 back to the extraction staging area 53. The individual pipettes 2a, 2b, 2c, 2d are preferably configured with high-precision liquid level detectors. The sampling module 1 is then moved on the working rails 50 beneath the pipette assembly 2 in the working area 49 such that predetermined sample containers 14 are positioned under the pipette assembly 2. The controller arranges the sampling module 1 beneath the pipette assembly 2 such that predetermined or known sample containers 14 with known samples therein are positioned beneath the pipette assembly 2 for sampling (FIG. 6C). The pipette assembly 2 is moved vertically toward the appropriate sample containers 14 such that the pipette tips are positioned in the sample containers 14 and the samples are drawn out of the sample containers 14 into the individual pipettes 2a, 2b, 2c, 2d. The pipette assembly 2 is subsequently moved by the controller away from the sample containers 14 with the samples held in the individual pipettes 2a, 2b, 2c, 2d. This linear and generally vertical movement of the pipette assembly 2 relative to the sample containers 4 limits mechanical vibrations during transfer of the sample and movement of the pipette assembly 2 over the containers 14, thereby reducing potential cross-contamination by a portion of the sample inadvertently falling into an incorrect sample container 14. The sampling module 1 is then moved away from the working area 49 and back into the sample area 48.

Referring to FIGS. 6A-7B, the extraction module 11 is then moved from the extraction staging area 53 into the working area 49 such that the extraction station 10 is positioned below the pipette assembly 2. The controller controls the positioning of the pipette assembly 2 over the appropriate tube slots 20a in the extraction plate 20 and the extraction tubes 22a. The reaction mixture 27 with the biological sample therein is transferred from the pipettes 2a, 2b, 2c, 2d into the appropriate extraction tubes 22. The reaction mixture 27 is retained in the extraction tube 22 by the flow resistant barrier 57 (FIG. 9A). The pipette assembly 2 is then moved upwardly out of the appropriate extraction tubes 22 and the extraction module 11 is moved on the working rails 50 from the working area 49 back into the extraction staging area 53 (FIG. 6D). The tips on the individual pipettes 2A, 2B, 2C, 2D that are contaminated with the biological sample are stripped and dropped into a waste tips container 17 under the working area 49. The above steps are repeated until all of the samples are added into the individual extraction tubes 22 of the extraction plate 20.

Referring to FIGS. 2-6F, the loaded samples are then subjected to a buffer. From an initial position (FIG. 6A), the extraction module 11 moves from the extraction staging area 53 into the working area 49 such that mat pipette tip module 9 is positioned beneath the pipette assembly 2. The pipette assembly 2 is moved downwardly by the controller such that the individual pipettes 2a, 2b, 2c, 2d engage with tips from the pipette tip module 9 that are secured thereto and the pipette assembly 2 is subsequently directed by the controller to move away from the pipette tip module 9. The extraction module 11 is moved in the working area 49 such that the buffer module 8 is moved beneath the pipette assembly 2 and the pipette tip assembly 2 is moved downwardly toward the buffer module 8. The buffer, preferably a lysis buffer, is drawn out of the buffer module 8 by the individual pipettes 2a, 2b, 2c, 2d and the pipette assembly 2 is moved away from the buffer module 8. The extraction station 10 with the biological materials positioned in the extraction tubes 22 is moved under the pipette assembly 2 and buffer is introduced into each one of the extraction tubes 22, preferably each of the ninety-six (96) extraction tubes in the eight by twelve (8×12) matrix. The extraction module 11 is then moved out the working area 49 and into the extraction staging area 53. The tips used with the buffer process on the pipette assembly 2 are then stripped and dropped into the waste tips container 17 beneath the working area 49. These steps are repeated until buffer is added into each one of the extraction tubes 22 in the extraction station 10.

The extraction module 11 is then moved from the extraction staging area 53 back into the working area 49 such that the pipette module 9 is positioned under the pipette assembly 2. The pipette assembly 2 moves downwardly toward the pipette tip module 9 to engage new pipette tips and subsequently moves away from the pipette tip module 9. One of the buffer containers 39 is then moved under the pipette assembly 2, the buffer is aspirated and the buffer container 39 is returned to its original position by moving the extraction module 1 from the working area 49 into the extraction staging area 53. The extraction station 10 is then moved under the pipette assembly 2 and the aspirated buffer with the magnetic beads 29 therein is added to the extraction tubes 22 with the biological material therein. The extraction module 11 is moved from the working area 49 into the extraction staging area 53 and the tips on the individual pipettes 2a, 2b, 2c, 2d are stripped and extracted into the waste tips container 17 beneath the working area 49. These steps are repeated until the buffer is added into each of the extraction tubes 22 with biological material therein.

Referring to FIGS. 7A-10, the buffer sample with the magnetic beads 29 or the reaction mixture 27 is then heated by the heating plate 33 and heating rods 34. In a particular process, the mixture is heated to a predetermined temperature, preferably between twenty-five and eighty degrees Celsius (25-80° C.) and incubated for approximately five to thirty minutes (5-30 min.). The reaction mixture 27 is concurrently and/or subsequently stirred by the magnetic beads 29 by applying alternate magnetic fields to the extraction tubes 22 with the electromagnets 30. Specifically, alternate current is applied to the electromagnets 30, thereby applying alternating magnetic fields to the individual extraction tubes 22 and causing the magnetic beads 29 to stir or spin within the extraction tubes 22. This process is in contrast to typical sample preparation processing where the tubes or plate holding the tubes are mechanically vibrated, spun or rotated to stir the reaction mixture 27. The prior art process may involve a shaker, which can create and disburse contaminating droplets of samples into the air, which is undesirable. During the magnetizing process, the appropriate nucleic acid, protein or other material is attracted to the magnetic beads 29 and becomes trapped on the outer surfaces of the magnetic beads 29. The magnetic beads 29 with appropriate nucleic acid or other material captured on external surfaces are drawn to the sides of the extraction tubes 22 by the electromagnets 30 (FIG. 9B). Following this heating, mixing and magnetizing, the reaction mixture 27 is converted to a waste liquid 28 with the amplified nucleic acid or other material adhered to the external surfaces of the magnetic beads 29. The waste liquid 28 is thereby extracted from the amplified nucleic acid.

Referring to FIGS. 6F and 9B-9E, the extraction station 10 is then moved beneath the aeration pipetter module 3. The aeration pipetter module 3 is moved downwardly such that the aeration tips 3a are positioned in the open top tube end 22b of the appropriate extraction tubes 22. When the aeration pipetter module 3 is moved downwardly into contact with the top tube end 22b of the extraction tubes 22, an aeration cap 3b associated with the aeration tips 3a preferably seals the top tube end 22b. Pressurized gas is introduced into the extraction tubes 22 through the aeration tips 3a to apply a predetermined pressure greater than atmospheric pressure to the waste liquid 28 and the waste liquid 28 is forced through the flow resistant barrier 57 into the waste tank 21. Forcing the waste liquid 28 through the flow resistant barrier 57 eliminates the requirement to remove the waste liquid 28 out of the top end of the extraction tubes 22, which is prevalent in prior art systems, and, thereby, reduces potential contamination of samples in adjacent extraction tubes 22. The magnetic beads 29 with the nucleic acid or other material adhered thereto are retained in the extraction tube 22 when the waste liquid 28 is expelled from the bottom tube end 22C into the waste tank 21. The aeration pipetter module 3 is then moved by the controller upwardly and out of contact with the extraction tubes 22. These steps may be repeated several times by adding additional buffer or washer buffer into the extraction tubes 22, heating, magnetizing, spinning and expelling the waste liquid 28 as desired by the user or as appropriate for the particular amplification of the nucleic acid.

New buffer tips are loaded onto the pipette assembly 2 and an elution buffer is loaded into each of the extraction tubes 22. The buffer is heated by the heating plate 33 and heating rods 34, preferably for approximately ten minutes (10 min.) and the mixture is stirred by applying magnetic field to the magnetic beads 29. The beads 29 are magnetized to the wall of the extraction tubes 22 and the purified nucleic acid is eluded from the beads 29.

The prepared samples in the ninety-six (96) well extraction plate 20 with the extraction tubes 22 associated therewith may then be moved to the sealing area 59 by the robotic system 5. The heat sealing module 6 is solidly sealed to avoid leakage from the wells during transportation, during analytic processing and following sample handling. The sealed extraction plate 20 is transferred into the isolation chamber 61 by opening the appropriate isolation door 61a. The air pressure of the connecting chambers is kept to avoid air flowing between the sealing area 59 and the isolation chamber 61. The sealed extraction plate 20 is delivered into the isolation chamber 61 and the appropriate isolation door 61a is quickly closed. Air in the isolation chamber 61 is pumped through and exits via high-efficiency particulate air ("HEPA") filters to eliminate undesirable airborne molecules. The sealed extraction plate 20 is decontaminated and the opposing isolation door 61a is opened to transfer the extraction plate 20 into the processing chamber 62. The air pressure of the connecting isolation and processing chambers 61, 62 is maintained to limit or avoid airflow between the isolation and processing chambers 61, 62. The decontaminated and sealed extraction plate 20 is delivered into the processing chamber 62 and the isolation door 61a is quickly shut.

This process may be ongoing while the pipette assembly 2, sampling module 1 and extraction module 11 continue to further operate, as is described above. This process, particularly based on the one-directional liquid flow in the extraction tubes 22 and the one-directional or substantially linear movement of the other related components, such as the movement of the extraction, module 11 on the working rails 50, the movement of the sampling module 1 on the working rails 50, the movement of the extraction support 55 on the extraction rails 56, the movement of the sample plate 16 on the sample rails 52, the movement of the pipette assembly 2 relative to the vertical support 46 and the movement of the individual sample holders 15a-15h relative to the sample plate 16 limit complicated, jerky, flow of the waste liquid upwardly out of the sample tubes and potentially contamination promoting movements present in prior art sample preparation systems. The described system and method, therefore, reduce numerous instances of potential contamination between various biological samples and waste fluids that can produce inaccurate test results and result in failed tests, which would have to be repeated and significantly and negatively impact testers, care providers, and patients.

Systems and methods according to embodiments of the invention can be used to prepare different biological samples for various analytical procedures. Examples of such biological samples include, but are not limited to, blood, serum, plasma, urine, saliva, feces, organ tissues, etc., preferably a biological specimen from a patient. Depending on the need, the processed sample can contain one or more isolated or enriched biological molecules that can be analyzed, detected or quantified in subsequent procedures. For example, a biological sample (such as a biological specimen from a subject) can be processed in a system of the invention to obtain a processed sample containing isolated or enriched nucleic acids, and the processed sample can be used for amplifying, detecting or quantifying one or more nucleic acids of interest, e.g., as the template in a PCR reaction, or in a hybridization processing using one or more chemiluminescent-labeled nucleic acids. In a preferred embodiment, a method according to an embodiment of the invention further comprises detecting or quantifying a nucleic acid in the processed sample using a PCR or a chemiluminescent assay. In another example, a biological sample (such as a biological specimen from a subject) can be processed in a system of the invention to obtain a processed sample containing peptides or proteins, and the processed sample can be used in an immunoassay, such as a radio immuno assay, ELIS A, immunofluorescence assay, or chemiluminescence immunoassay, for detecting or quantifying one or more peptides or proteins of interest. In a preferred embodiment, a method according to an embodiment of the invention further comprises detecting or quantifying a peptide or polypeptide in the processed sample using an ELISA, an immunofluorescence assay, or a chemiluminescence immunoassay (CLIA), more preferably, a CLIA. The CLIA is a more sensitive alternative to ELISA, which involves the generation of electromagnetic radiation as light by the release of energy from a chemical reaction and the measurement of light intensity, e.g., using a photomultiplier or photodiode and the associated electronics to convert and record signals. Known methods and reagents for detecting or quantifying biological molecules, such as the PCR, ELISA, immunofluorescence, assay or CLIA. Procedures can be used in the invention in view of the present disclosure.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present disclosure.

We claim:

1. A biologic sample preparation system that prepares biologic samples for analytic processing, the system comprising:
   a) a horizontal frame defining a sample area on a right side of the horizontal frame, an extraction staging area on a left side of the horizontal frame, and a working area in a middle section, between the sample area and the extraction staging area of the horizontal frame;
   b) a pipette assembly movably mounted to a vertical support attached to the horizontal frame and movable in a direction perpendicular to the horizontal frame during operation, wherein the working area is below the pipette assembly;

c) a sample module configured to move horizontally on the horizontal frame at least from the sample area to the working area and back to the sample area, wherein the sample module comprising a sample plate and a plurality of sample holders configured for a linear movement relative to the sample plate, sample containers mounted to the sample plate; and a sample bed;

d) an extraction module configured to move horizontally on the horizontal frame at least from the extraction staging area to the working area and back to the extraction staging area, the extraction module comprising:
 i. an extraction bed;
 ii. an extraction plate having a plurality of extraction tube holes configured to receive a plurality of extraction tubes containing a reaction solution that comprise biologic samples, buffers, and magnetic beads for analytic processing, wherein each extraction tube has a top tube end and a bottom tube end, tube sides, and a flow resistant barrier positioned relative to the bottom tube end;
 ii. an extraction station comprising:
  a waste housing, a waste tank, and a magnet and heat module, wherein the waste tank is slidably and removably mounted to the waste housing for disposal of a waste liquid that accumulates in the waste tank, and wherein the magnet and heat module comprises a core plate, a heating plate, a plurality of heating rods, and a plurality of electromagnets, wherein the plurality of electromagnets are configured to be positioned relative to the tube sides and the bottom tube end of each extraction tube and configured to apply a magnetic field to the extraction tubes, causing magnetic beads to stir or spin within each extraction tube, wherein during a magnetizing process, nucleic acids and proteins of biologic samples are attracted to the magnetic beads and become trapped on outer surfaces of the magnetic beads, and wherein the magnetic beads are drawn to tube sides of the extraction tubes by the plurality of electromagnets, thereby a waste liquid is separated from the reaction solution;

e) an aeration pipette module configured to apply a pressurized gas into each extraction tube to overcome the flow resistant barrier and force the waste liquid out of each extraction tube from a bottom opening of each extraction tube and into the waste tank, while retaining the magnetic beads with nucleic acids and proteins adhered on outer surfaces of the magnetic beads in each extraction tube, and f) a controller configured to control movement and operation of the pipette assembly, the extraction module, the sample module, and the aeration pipette module, to separate nucleic acids and proteins from biologic samples and generate a waste liquid that flows downward into the waste tank, and nucleic acids and proteins are capable of being recovered without any cross contamination.

2. The system of claim 1, wherein the extraction module further comprising:
 a) an extraction support movably mounted to the on a set of extraction rails and configured for linear movement of the extraction support on the set of extraction rails relative to the horizontal frame;
 b) a pipette tip module mounted adjacent the extraction station on the extraction support, and
 c) a buffer module mounted to the extraction support relative to the pipette tip module.

3. The system of claim 1, comprising the plurality of extraction tubes being located in the plurality of extraction tube holes, wherein the flow resistant barrier comprises a puncturable polymeric film configured to prevent flow of the biologic samples through the bottom tube end under a pressure less than or equal to atmospheric pressure and puncturable polymeric film is configured to permit the flow of the biologic samples through the polymeric film when the flow of biologic samples is subjected to a pressure greater than atmospheric pressure.

4. The system of claim 1, comprising the plurality of extraction tubes being located in the plurality of extraction tube holes, wherein each of the plurality of extraction tubes include a vent tubes with a micro-hole configured to prevent the biologic samples from flowing through the flow resistant barrier under pressure at and less than atmospheric pressure and to permit flow of the waste liquid from the bottom tube end.

5. The system of claim 1, comprising the plurality of extraction tubes being located in the plurality of extraction tube holes, wherein the flow resistant barrier comprises a capillary integrally formed in the vert tube at the bottom tube end.

* * * * *